United States Patent [19]

McNabb

[11] Patent Number: 5,659,092
[45] Date of Patent: Aug. 19, 1997

[54] PURIFICATION PROCESS

[75] Inventor: Andrew J. McNabb, Lake Jackson, Tex.

[73] Assignee: BASF Corporation, Mount Olive, N.J.

[21] Appl. No.: 483,527

[22] Filed: Jun. 7, 1995

[51] Int. Cl.$^6$ .................................................. C07C 27/26
[52] U.S. Cl. ................................. 568/868; 568/872
[58] Field of Search ............................ 568/822, 832, 568/868, 872, 833

[56] References Cited

U.S. PATENT DOCUMENTS 3,855,320  12/1974  Leach .
3,933,930  1/1976   Doughtery .
4,096,036  1/1978   Liu .
4,935,552  6/1990   Child .
5,155,182  10/1992  Burba .

Primary Examiner—Jose G. Dees
Assistant Examiner—Karl Puttlitz
Attorney, Agent, or Firm—Nixon & Vanderhye P.C.

[57] ABSTRACT

The present invention relates, in general, to a purification process, and particular, to a process of removing cyclic alkane alcohols from compositions comprising linear alkane alcohols.

10 Claims, 1 Drawing Sheet

PURIFICATION PROCESS

TECHNICAL FIELD

The present invention relates, in general, to a purification process, and in particular, to a process of removing cyclic alkane alcohols (including mono, di and poly alcohols) from compositions comprising linear alkane alcohols.

BACKGROUND

Certain alkane alcohols, such as hexanediols, are valuable intermediate products in the chemical industry. 1,6 Hexanediol finds application in a variety of polymeric systems and can be used in the synthesis of specialty chemicals. The terminal location of the hydroxyl groups of 1,6 hexanediol results in a rapid and simultaneous reaction in the formation of numerous disubstituted products.

1,6 Hexanediol is used in the production of polyesters for polyurethane elastomers, coatings, adhesives, and polymeric plasticizers. In these end-use areas, it contributes significantly to many high-performance characteristics such as hydrolytic stability, high flexibility, good adhesion and surface hardness.

Cyclohexanediols, especially the 1,4 cis and 1,4 trans forms, constitute impurities in hexanediol production processes. The presence of the cyclic diols may reduce flexibility of coatings prepared from resins resulting from the reaction of hexanediols with acids. Uneven distribution of cyclohexanediols in the resin can also result in the uneven distribution of cyclohexanediol polymers and thus the potential for slightly different properties in various parts of the resulting resin. Removal of cyclohexanediols allows formation of a more consistent resin.

Prior to the present invention, difficulties were encountered in removing, for example, cycloalkanediols from compositions comprising the linear counterparts. The difficulties resulted from the fact that the boiling points of the linear and cyclic forms are sufficiently similar to make separation by distillation difficult. The present invention overcomes that problem by providing a method of converting, for example, a cyclic alkanediol to a compound having a boiling point that is sufficiently different from that of the corresponding linear alkanediol to permit separation by distillation.

OBJECTS AND SUMMARY OF THE INVENTION

It is a general object of the invention to provide a method of separating cyclic and linear forms of alkane alcohols, particularly, alkanediols.

It is a specific object of the invention to provide a simple and efficient method of converting cyclic alkanediols to compounds that boil at a significantly different temperature.

In accordance with the foregoing objectives, the present invention provides a method of separating a cyclic alkanediol or polyol from the linear form of the diol or polyol. The method comprises contacting a composition containing the cyclic alkanediol or polyol and the linear form of the diol or polyol with an acidic resin under conditions such that the cyclic alkanediol or polyol is converted to a compound having a boiling point sufficiently different (eg by at least about 10 degrees C.) to permit separation of the compound from the linear form of the diol or polyol by, for example, distillation.

Further objects and advantages of the present invention will be clear from the description that follows.

DETAILED DESCRIPTION OF THE INVENTION

Figure 1:
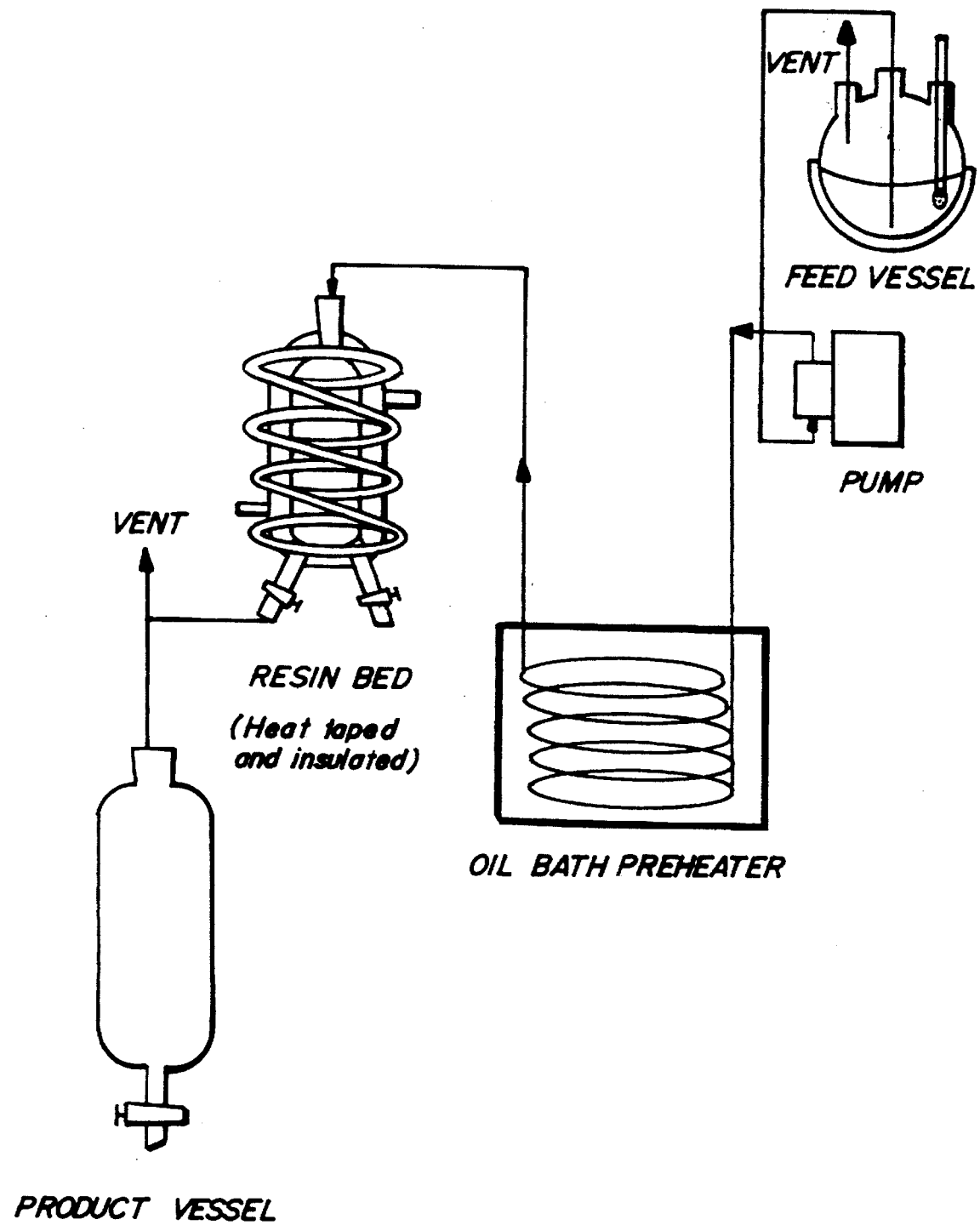
FIG. 1 shows a set up that can be used to effect the process of the invention.

The present invention relates to a method of separating cyclic alkane alcohols, particularly, cyclic alkanediols, from linear alkane alcohols (e.g., diols). More specifically, the invention relates to a method of converting cyclic alkane diols, particularly, cyclic $C_3$–$C_8$ alkane diols, from linear $C_3$–$C_8$ alkane diols. While the conversion of diols (eg cyclic propane, butane, pentane, hexane, heptane and octane diols) is of particular importance from the standpoint of resin production, the present method has general applicability to alcohol (including polyol) purification processes.

In accordance with the present invention, the composition to be treated is contacted with an acidic resin under conditions such that cyclic alkane alcohols in the composition are converted to compounds having boiling points sufficiently different from the corresponding linear alkane alcohol to permit separation by distillation. For example, a crude composition of hexanediol (particularly, 1,6 hexanediol) can be contacted with an acidic resin (e.g., a sulfonated, divinylbenzene/styrene copolymer) (H ion form) such as Rohm and Haas Amberlyst 15 or Amberlyst 36, or coparable resin, under conditions such that cyclohexanediol present in the crude hexanediol composition is converted to a compound having a boiling point sufficiently different from the linear hexanediol to permit separation by distillation. Boiling point differences of about 10 degrees C. are sufficient to permit fractionation by distillation.

The process of the invention can be carried out using conventional batch or continuous distillation processes. The distillation and acid resin treatment can be combined in a variety of manners depending, for example, on the starting composition and the result sought. For example, the starting composition can be contacted with acidic resin (eg in a packed bed or slurry) at an elevated temperature (eg, about 90 degrees C. to about 180 degrees C., preferably about 100 degrees C. to about 150 degrees C.) and the resulting mixture subjected to distillation (eg batch distillation). The distillation fraction containing the compound sought (eg the linear alkane alcohol) can then be further processed as appropriate. Alternatively, distillation (eg batch) can be carried out prior to the acid resin treatment and that fraction containing the alkane alcohol of interest subjected to acid resin treatment, followed by further distillation fractionation.

FIG. 1 describes a set up that can be used to carry out the process of the invention.

The conditions under which the process of the invention is carried out will vary with the nature of the involved alcohol, the resin used, the result sought, etc. Optimum conditions, including temperature of the starting composition, volume of the resin, temperature of the resin and residence time of the composition in the resin, can be readily established.

While not wishing to be bound by theory, it is believed that the acidic conditions provided by the acid resin of the invention result in acid catalyzed dehydration of the cyclic alkane alcohol. The selectivity of the reaction is believed to be derived from the greater reactivity, for example, of a secondary alcohol (relative to a primary alcohol) to acid catalyzed reactions.

Certain aspects of the present invention are described in greater detail in the non-limiting examples that follow.

EXAMPLE 1

A sample of crude 1,6 hexanediol was analyzed and found to contain 2.4% of the 1,4 cis and trans cyclohexanediols. A mixture of 200 g of crude 1,6 hexanediol and 10 g of Amberlyst 15 resin was heated to 135° C. for one hour. Analysis of the pot residue indicated that the amount of 1,4 cis and trans cyclohexanediols had been reduced to less than 0.8%.

EXAMPLE 2

A sample of crude 1,6 hexanediol was analyzed and found to contain 2.4% of the 1,4 cis and trans cyclohexanediols. A mixture of 200 g of crude 1,6 hexanediol and 10 g of Amberlyst 15 resin was heated to 135° C. for two hours. Analysis of the pot residue indicated that the amount of 1,4 cis and trans cyclohexanediols had been reduced to less than 0.5%.

Any document cited above is hereby incorporated in its entirety by reference.

One skilled in the art will appreciate from a reading of this disclosure that various changes in form and detail can be made without departing from the true scope of the invention. One skilled in the art will also appreciate that standard techniques can be used to determine the amount of, for example, cyclic alkane alcohol present.

What is claimed is:

1. A method of separating a cyclic alkane diol or polyol from a linear form of said diol or polyol comprising contacting a composition containing said cyclic alkane diol or polyol and said linear form of said diol or polyol with an acidic resin under conditions such that said cyclic alkane diol or polyol is converted to a compound having a boiling point sufficiently different from that of said linear form of said diol or polyol to permit separation of said compound from said linear form of said diol or polyol and separating said compound from said linear form of said diol or polyol.

2. The method according to claim 1 wherein said alkane diol or polyol is a $C_3$–$C_8$ diol.

3. The method according to claim 2 wherein said $C_3$–$C_8$ diol is a $C_6$ diol.

4. The method according to claim 3 wherein said $C_6$ diol is 1,6 hexanediol.

5. The method according to claim 1 wherein said acidic resin is a sulfonated copolymer.

6. The method according to claim 5 wherein said copolymer is a divinylbenzene/styrene copolymer.

7. A method of converting a cyclic alkane diol or polyol to a compound having a boiling point sufficiently different from said a linear form of said diol or polyol to permit separation of said compound from said linear form of said diol or polyol comprising contacting said cyclic alkane diol or polyol with an acidic resin under conditions such that said conversion is effected.

8. The method according to claim 7 wherein said cyclic alkane diol or polyol is a diol.

9. The method according to claim 8 wherein said cyclic alkane diol is cyclohexanediol.

10. The method according to claim 9 wherein said linear form of said cyclohexanediol is 1,6-hexanediol.

* * * * *